United States Patent [19]

Kawai et al.

[11] Patent Number: 4,746,512
[45] Date of Patent: May 24, 1988

[54] ANTICARIOGENIC OR ANTIPERIODONTITIC AGENT

[75] Inventors: Yasuo Kawai, Atsugi; Kazuoki Ishihara, Tokyo, both of Japan

[73] Assignee: Kabushiki Kaisya Advance Kaihatsu Kenkyujo, Tokyo, Japan

[21] Appl. No.: 709,668

[22] Filed: Mar. 8, 1985

[30] Foreign Application Priority Data

Mar. 9, 1984 [JP]   Japan ................................. 59-43829
Oct. 9, 1984 [JP]   Japan ................................ 59-210536

[51] Int. Cl.$^4$ ..................... A61K 39/09; A61K 39/02; C12N 1/20; A01N 63/02
[52] U.S. Cl. ........................................ 424/92; 424/93; 424/49; 424/50; 435/253
[58] Field of Search .................... 435/253; 424/92, 93, 424/49, 50

[56] References Cited

U.S. PATENT DOCUMENTS 4,448,768  5/1984  Colman et al. ....................... 424/92

FOREIGN PATENT DOCUMENTS

A-0-058575  6/1982  European Pat. Off. .
59-220191  11/1984  Japan .

OTHER PUBLICATIONS

Ikeda et al., (Abstract), Infect. Immun., 35(3), pp. 861–868, (1982).
Ozeki, M., (Abstract), Aichi-Gakuin J. Dent Sci., 19(4), pp. 22–56, (1982).

Primary Examiner—Blondel Hazel
Attorney, Agent, or Firm—Finnegan, Henderson, Farabow, Garrett and Dunner

[57] ABSTRACT

An anticariogenic or antiperiodontitic agent containing, as an active component, the bacterial cells and/or water-soluble extracts of a microorganism belonging to the genus Streptococcus or the genus Lactobacillus having antibacterial activity against Streptococcus mutans or the genus Bacteriodes.

This anticariogenic or antiperiodontitic agent has strong inhibitory effects on the growth of Streptococcus mutans causing dental caries and Bacteroides causing periodontitis and has no influence on intestinal microflora when orally administered.

2 Claims, 3 Drawing Sheets

ANTICARIOGENIC OR ANTIPERIODONTITIC AGENT

BACKGROUND OF THE INVENTION

1. Field of the Invention

The present invention relates to an anticariogenic or antiperiodontitic products such as beverages and foods which have an anticariogenic or antiperiodontitic activity.

2. Description of the Related Art

Several kinds of bacteriocins and other substances acting in a similar way to anti-bacterial substances against Streptococcus mutans, which is a major pathogen of dental caries, have been proposed, and several kinds of antibiotics are known, such as tetracyclines and others, against genus Bacteroides causing periodontitis. However, their side-effects, for example, the influence of these substances on the intestinal microflora, are not yet fully understood and, thus, these substances are not used in practice, because it has not been proved that they are safe for daily usage.

SUMMARY OF THE INVENTION

Accordingly, the objects of the present invention are to eliminate the above-mentioned possible side-effects in the prior art and to provide an anticariogenic or antiperiodontitic agent or composition having strong inhibitory effects on the growth of Streptococcus mutans causing dental caries and Bacteroides causing periodontitis and having no influence on intestinal microflora when orally administered.

Other objects and advantages of the present invention will be apparent from the following description.

In accordance with the present invention, there is provided an anticariogenic or antiperiodontitic agent or composition containing, as an active component, the bacterial cells and/or water-soluble extracts of a microganism belonging to the genus Streptococcus or the genus Lactobacillus having antibacterial activity against Streptococcus mutans or the genus Bacteroides.

BRIEF DESCRIPTION OF THE DRAWINGS

The present invention will be better understood from the description set forth below with reference to the drawings, in which.

DESCRIPTION OF THE PREFERRED EMBODIMENT

Figure 1:
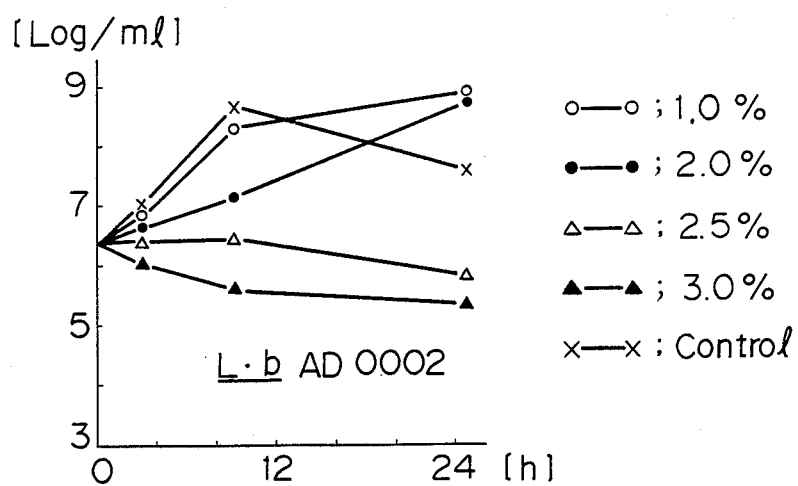
FIG. 1 is a graphical drawing illustrating the inhibitory effects of the hot water-soluble extracts of a strain L. fermentum AD 0002 (i.e., FERM BP-715) on the growth of S. mutans in various concentrations.

The present inventors have found that the cells of intestinal (lactic acid) bacteria isolated from healthy humans, and their soluble extracts, have strong inhibitory effects on the growth of S. mutans causing dental caries and Bacteroides causing periodontitis, and that these lactic acid bacteria and water-soluble extracts have shown no toxicity in animal experiments and have no influence on intestinal microflora when orally administered.

The types and bacteriological characteristics, the preparation of the anticariogenic or antiperiodontitic products, the anti-bacterial activity, the forms in practical use, and the like, of the bacteria and water-soluble extracts according to the present invention will now be described in detail hereinbelow.

Microorganisms

Microorganisms suitable for use in the preparation of the bacterial cell product according to the present invention are those belonging to the genus Streptococcus and Lactobacillus, especially, S. faecius, S. equinus, L. fermentum, L. salivarius, and the like.

Typical examples of such microorganisms were deposited on Mar. 8, 1984 in the Fermentation Research Institute (FRI) in Japan (all numbers quoted as "FERM-P" in Table 1 refer to the deposition numbers of said Institute) and transferred to the Fermentation Research Institute (FRI) (i.e., International Depository Authority under Budapest Treaty in Japan) as the FERM-BP deposition numbers shown in Table 1 under the Budapest Treaty on the International Recognition of the Deposit of Microorganisms for the Purpose of Patent Procedure:

TABLE 1

| Strains | Deposition number | |
|---|---|---|
| L. salivarius AD0001 | FERM P-7537 | FERM BP-713 |
| L. fermentum AD0002 | FERM P-7539 | FERM BP-715 |
| S. equinus AD8005 | FERM P-7540 | FERM BP-716 |
| S. faecium AD1051 | FERM P-7536 | FERM BP-712 |
| S. faecium AD1050 | FERM P-7538 | FERM BP-714 |

The screening methods and the typical microbiological properties of the above-exemplified strains according to the present invention can be summarized as follows:

1. Screening methods

The screening of the microorganisms can be carried out by a method disclosed by Watanabe, T. et al., in "Studies on Streptococci. I. Distribution of Fecal Streptococci in Man, Microbiol, Immunol. 25, 257–269 (1981)".

That is, as described in this literature, 10-fold diluted feces obtained from healthy humans were smeared on KMN agar (for streptococci) or LBS agar (for lactobacilli) and were aerobically (for streptococci) or anaerobically (for lactobacilli) cultivated at 37° C. for 48 to 72 hours. The formed colonies were counted and were randomly isolated. The colony type and catalase-negative and Gram-positive spherical and rod-shaped bacteria were determined. The isolates were identified and classified by examining physiological, biochemical, and serological properties.

2. Identification of lactic acid bacteria isolated from human feces

The morphology of the colonies formed on the KMN agar (Table 2) and LBS agar (Table 3), the selected media for the isolation of the genus Streptococcus and Lactobacillus, respectively, was examined. Then, the isolated bacteria were identified by the Gram stain, the cell shape, and the physiological, biochemical, and serological properties. The following articles were used during this identification procedure:

(1) Clin. Bacteriol. 2, 197–239 (1975)
(2) Japan. J. Bacteriol. 24, 261–280 (1969)
(3) Microbiol. Immunol, 25, 257–269 (1981)
(4) J. Bacteriol. 86, 1275–1282 (1963)
(5) Bergey's Manual of Determinative Bacteriology, 8th ed., 490–509 (1974)

TABLE 2

| KMN agar (Red-Kanamycin-Milk agar) | | |
| --- | --- | --- |
| Tryptose | 15 g | pH 6.5 |
| Meat extract | 3 g | |
| Sodium azide | 0.2 g | Autoclaved at 121° C. for 10 min. |
| NaCl | 5 g | |
| Agar | 18 g | |
| Distilled water | 800 ml | |
| Skim milk | 16 g | |
| Neutral red | 40 mg | Heated at 100° C. for 1 hr. |
| Kanamycin | 24 mg | |
| Distilled water | 200 ml | |

After sterilization, both parts are mixed together.

TABLE 3

| LBS agar | |
| --- | --- |
| LBS agar powder (BBL) | 84 g |
| Tomato juice | 200 ml |
| Acetic acid | 1.32 ml |
| Distilled water | 800 ml | pH 5.5 ± 0.2
Autoclaved at 115° C. for 15 min.

The typical bacteriological properties used as criteria for the identification of the exemplified strains according to the present invention are summarized in Tables 4 and 5.

TABLE 4

| Characteristics | AD0001 | AD0002 |
| --- | --- | --- |
| Shape of colony on LBS agar | Protuberant, smooth, white, glistening | Protuberant, smooth, white, glistening |
| Gram stain | + | + |
| Shape of cell | short rod, chain | short rod, chain |
| Catalase | − | − |
| Gas production | − | − |
| Growth at | | |
| 15° C. | − | − |
| 45° C. | + | + |
| Litmus milk* | ACR | − |
| Acid production from | | |
| Arabinose | − | + |
| Xylose | − | + |
| Ribose | − | + |
| Glucose | + | + |
| Mannose | + | − |
| Galactose | + | + |
| Saccharose | + | + |
| Maltose | + | + |
| Cellobiose | − | − |
| Lactose | + | + |
| Trehalose | + | + |
| Melibiose | + | + |
| Raffinose | + | + |
| Melezitose | − | − |
| Mannitol | + | − |
| Sorbitol | + | − |
| Esculin | + | − |

TABLE 4-continued

| Characteristics | AD0001 | AD0002 |
| --- | --- | --- |
| Salicin | + | − |
| Amygdalin | − | − |
| Identification | L. salivarius | L. fermentum |

+: positive, −: negative,
*litmus milk, A: acid, C: coagulation, R: reduction

TABLE 5

| Characteristics | AD8005 | AD1051 | AD1050 |
| --- | --- | --- | --- |
| Shape of colony on KMN agar | Flat, pellucid, red | Protuberant, smooth, white, glistening | Protuberant, smooth, white glistening |
| Gram stain | + | + | + |
| Shape of cell | coccus, chain | coccus, chain | coccus, chain |
| Catalase | − | − | − |
| Growth at | | | |
| 10° C. | + | + | + |
| 45° C. | + | + | + |
| 50° C. | − | + | − |
| Growth in culture medium at pH 9.6 | − | + | + |
| Methylene blue reduction | − | + | + |
| Growth in culture medium containing NaCl (6.5%) | − | + | + |
| Growth in culture medium containing bile (40%) | + | + | + |
| Hydrolysis of starch | − | − | − |
| Polysaccharide formation from saccharose | − | − | − |
| Production of ammonia | − | + | + |
| Growth in culture medium containing tellurite | − | − | − |
| Growth in culture medium containing TTC *1 | − | − | − |
| Acid production from | | | |
| Arabinose | − | + | + |
| Melezitose | − | − | − |
| Sorbitol | − | − | + |
| Glycerol | − | − | − |
| Sorbose | − | − | + |
| Esculin | − | + | + |
| Lactose | − | + | + |
| Litmus milk *2 | − | − | ACR |
| Energy utilization | | | |
| Pyruvate | ND | − | − |
| Arginine | ND | − | − |
| Citrate | ND | − | − |
| Identification | S. equinus | S. faecium | S. faecium *3 |

+: positive, −: negative,
*1 TTC: 2,3,5-triphenyl tetrazolium chloride
*2 Litmus milk, A: acid, C: coagulation, R: reduction
*3 ND: not done
*4 Strain AD1050 was identified as S. faecium. However, this strain has properties of S. faecalis, for example, no growth at 50° C. and acid production from sorbitol.

3. Cultivation methods

The cultivation methods of these microorganisms are conventional as mentioned above. For example, the bacterial cells can be collected by stationary cultivations in Rogose broth medium consisting of the following composition under an aerobical condition, and can be harvested by centrifugation of the culture.

| Composition of Rogosa broth medium | |
| --- | --- |
| Trypticase (BBL) | 10 g |
| Yeast extract | 5 g |
| Tryptose | 3 g |
| KH$_2$PO$_4$ | 3 g |
| K$_2$HPO$_4$ | 3 g |
| Triammonium citrate | 2 g |
| Tween 80 | 1 g |

|  |  |
|---|---|
| Glucose | 20 g |
| Cystein hydrochloride | 0.2 g |
| Salt solution *1 | 5 ml |
| Distilled water | to 1 liter |
| (pH 7, autoclaved at 121° C. for 15 min) | |
| *1 MgSO$_4$—7H$_2$O | 11.5 g |
| FeSO$_4$—7H$_2$O | 0.68 g |
| MnSO$_4$—2H$_2$O | 2.4 g |
| Distilled water | 100 ml |

Preparation of anticariogenic and antiperiodontitic products

The dead cells having undergone various treatments, and the water-soluble extracts of the microorganisms used in the present invention and suitable for use as anticariogenic and antiperiodontitic agents, are typically prepared as follows:

1. Hot-water extraction

The harvested bacterial cells were suspended in water, and were heated at 80° C. to 130° C., preferably at 100° C. to 125° C., for several minutes to several hours with and without pressure. The water-soluble anticariogenically and antiperiodontitically active extracts were obtained by centrifugation, etc. to remove water-insoluble solids.

Physiological saline (0.85% NaCl, etc.), various kinds of pH-adjusted buffers, various kinds of salt solutions, water/alcohol (methanol, ethanol, etc.) >$\frac{1}{2}$ (w/w), and various aqueous solvents can be also used for the extraction. Moreover, the whole cell preparations heat-treated in hot-water as described above can be also used for suitable anticariogenic and antiperiodontitic agents of the present invention, as powder or other preparation forms, by lyophilization, drying in vacuo, and spray drying.

2. Sterilization

The cell preparations made by spray-drying or heat-treatment with other methods or sonication (for example, at 15 KC for 1 hour) can be also used for anticariogenic and antiperiodontitic agents of the present invention. And the water-soluble components of the sterilized cell preparations as shown above can be also used for anticariogenically and antiperiodontitically active fractions in the present invention.

Anticariogenic and antiperiodontitic activities

1. Antibacterial activity

As shown in the Examples, the anticariogenic and antiperiodontitic products of the present invention effectively depress or inhibit the growth of *S. mutans* which causes dental caries and Bacteroides which causes periodontitis.

Nevertheless, the products have selective and specific antibacterial spectra; that is, the products have substantially no inhibitory effects on the growth of the major lactic acid bacteria (*S. faecalis, S. faecium, L. fermentum, L. acidophilus, B. adolescentis, B. infantis, B. bifidum,* and *B. breve*) and *E. coli* of the intestinal bacteria.

2. Acute toxicity

As shown in the Examples, an LD50 value of the hot water-soluble extracts or the sterilized bacterial cells according to the present invention was >ca. 6 mg/mouse (intraperitoneal administration). Both the preparations according to the present invention were substantially nontoxic on oral administration.

Forms in practical use

The anticariogenic and antiperiodontitic products of the present invention can be practically used in the forms of, for example, tooth-paste, gargles, troches, chewing gum, and the like, and in the form of various kinds of anticariogenically and antiperiodontitically depressive and preventive foods and beverages added with the anticariogenic and antiperiodontitic products. The amount used in practical use is ca. 0.001% to 10% (w/w) in the form of the dried treated bacterial cells or the hot water-soluble extracts.

EXAMPLES

The present invention will now be further shown by, but is by no means limited to, the following Examples.

Example 1

Preparation methods

The lactic acid bacterial strains of the present invention were inoculated into 1000 parts by volume of Rogosa broth medium at a final concentration of $10^6$ viable cells/ml, and were stationarily incubated at 37° C. for 15 to 24 hours. Then, the bacterial cells were collected by centrifugation of the culture fluid. The separated cells were washed twice with 20 parts by volume of 0.85% NaCl solution by centrifugation. The centrifuged cells were then suspended in 1 part by volume of distilled water, and were autoclaved at 115° C. to 121° C. for 10 to 15 minutes. Finally, the autoclaved cells were centrifuged to obtain the supernatant, and the supernatant was lyophilized or heat-dried at 110° C. This dried extract was used for the growth inhibition tests.

The sterile solution of this extract (the extract was dissolved in water, the pH was adjusted to 7, and sterilization was done by autoclaving at 121° C. for 15 min or filtration with membrane filters) was added into the sterile Rogosa broth or Todd-Hewitt broth (note 1) together with sterile distilled water to adjust the concentration of the medium to one half and to adjust the concentration of the hot water-soluble extract. To this medium, *S. mutans* 8148 (supplied from the National Institute of Health, Japan) was inoculated at the viable cell concentration of $10^6$/ml. The viable cell number was enumerated periodically, for 0 to 24 hours after inoculation. In the controls, 0.85% NaCl solution was added instead of the extract.

Note 1: Todd-Hewitt broth medium

Dissolve 30 grams/liter distilled water of powder containing the following formula.

|  |  |
|---|---|
| Infusion from beef heart | 500 |
| Peptone | 20 |
| Dextrose | 2 |
| NaCl | 2 |
| Na$_2$HPO$_4$ | 0.4 |
| Na$_2$CO$_3$ | 2.5 |
| pH 7.8 | |

Autoclaved at 121° C. for 15 min. (Updyke et al. Appl. Microbiol. 2: 177 (1954))

The concentration of the hot water-soluble extracts in the extraction fluid is shown in Table 6.

TABLE 6

| | No. of viable cells at full growth | Concentration of cellular extracts *1 |
|---|---|---|
| L. fermentum AD0002 | 10^9.6 cells/ml | 2.0% |
| L. salivarius AD0001 | 10^9.2 cells/ml | 2.0% |
| S. faecium AD1050 | 10^9.1 cells/ml | 1.5% |
| S. equinus AD8005 | 10^8.7 cells/ml | 1.0% |
| S. faecium AD1051 | 10^8.9 cells/ml | 1.5% |

*1 Concentration of extracts from the cells suspended in 1/100 volume distilled water in the culture medium.

Results

Figure 2:
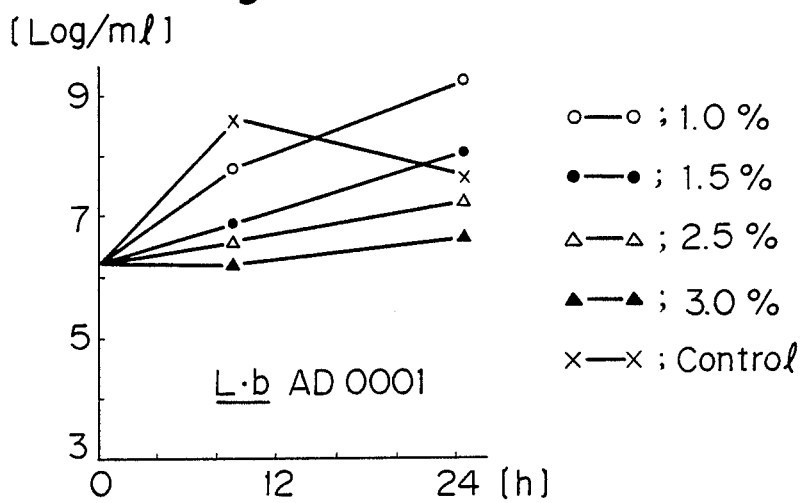
FIG. 2 is a graphical drawing illustrating the inhibitory effects of the hot water-soluble extracts of a strain L. salivarius AD 0001 (i.e., FERM BP-713) on the growth of S. mutans in various concentrations.
Figure 3:
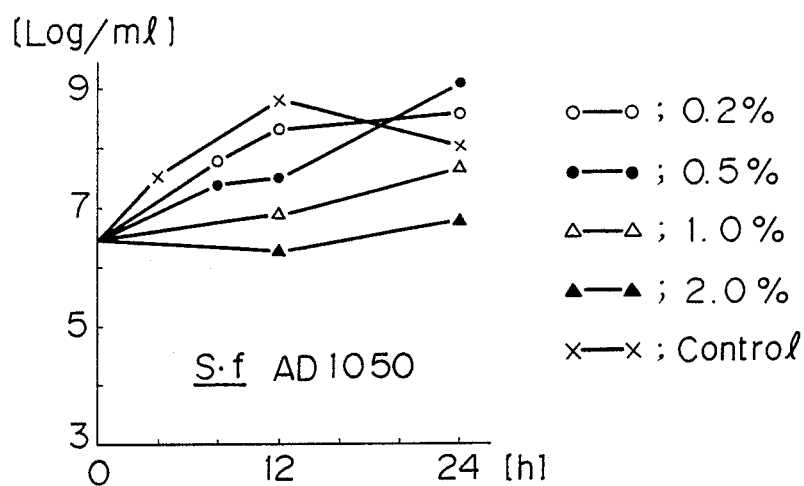
FIG. 3 is a graphical drawing illustrating the inhibitory effects of the hot water-soluble extracts of a strain S. faecium AD 1050 (i.e., FERM BP-714) on the growth of S. mutans in various concentrations.
Figure 4:
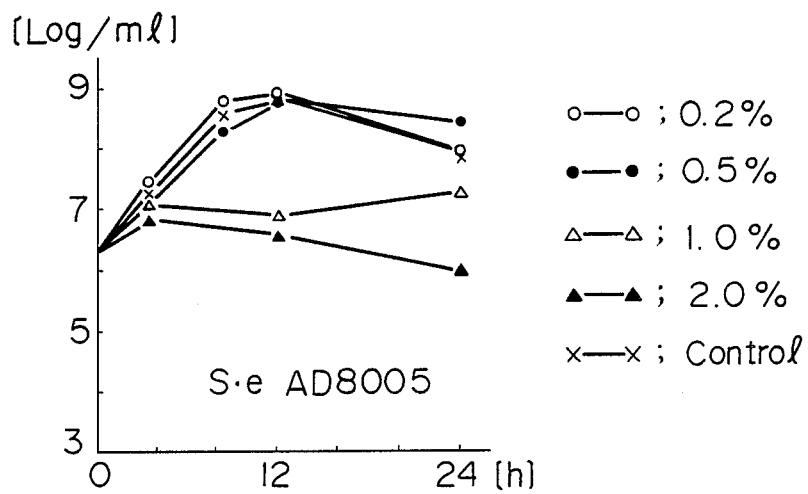
FIG. 4 is a graphical drawing illustrating the inhibitory effects of the hot water-soluble extracts of a strain S. equinus AD 8005 (i.e., FERM BP-716) on the growth of S. mutans in various concentrations.
Figure 5:
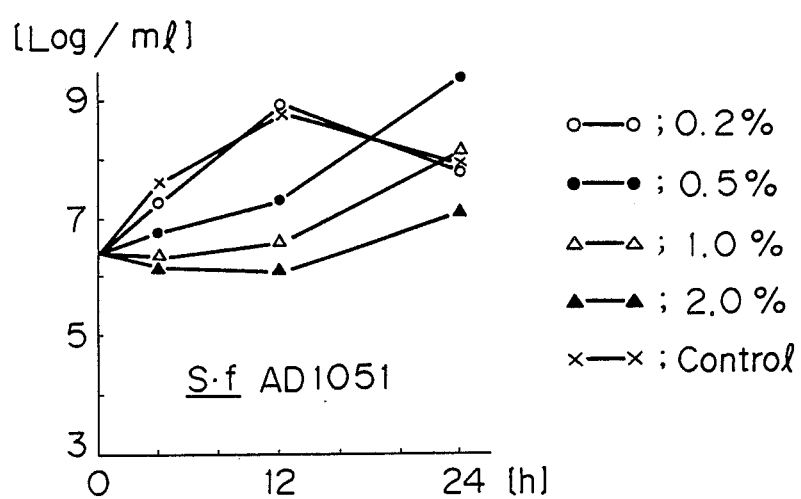
FIG. 5 is a graphical drawing illustrating the inhibitory effects of the hot water-soluble extracts of a strain S. faecium AD 1051 (i.e., FERM BP-712) on the growth of S. mutans in various concentrations.

As summarized in FIGS. 1 to 5, the inhibitory effect of the hot water-soluble extracts on the growth of *S. mutans* depended on the concentration of the extracts, in any strain of *Streptococcus faecium*, *Streptococcus equinus*, *Lactobacillus fermentum*, and *Lactobacillus salivarius*. The hot water-soluble extracts obtained from the *S. faecium* strain inhibited the growth of *S. mutans* completely for 24 hours, almost completely for 12 hours, and >95% for 12 hours at 2%, 1%, and 0.5% of the extracts, respectively. The hot water-soluble extracts obtained from *S. equinus* strain completely inhibited the growth of the *S. mutans* strain for 24 hours at 1% of the extracts, and the 2% concentration of the extracts showed a weak bactericidal effect on *S. mutans*. The hot water-soluble extracts obtained from the *L. fermentum* strain had a bactericidal effect on *S. mutans* at >2.5% of the extracts. The hot water-soluble extracts obtained from the *L. salivarius* strain inhibited completely the growth of *S. mutans* for 24 hours at 2.5% of the extracts, and inhibited >95% at 1.5% of the extracts. The influence of the hot water-soluble extracts obtained from these lactic acid bacteria on the cell division rate of the *S. mutans* strain is shown in Table 7. The hot water-soluble extracts greatly reduced the cell division rate at a concentration at which the extracts did not completely inhibit the growth.

The heat-treated whole cells and the other preparations of the present invention showed the same results as described above. In FIGS. 1 to 5, the ordinate indicates viable cell counts (log/ml) of *S. mutans*, the abscissa indicates the incubation time (hours), and the bacterial species are shown by initials.

TABLE 7

| Conc. of extracts | Strains | | | | |
|---|---|---|---|---|---|
| | L. fermentum AD0002 | L. salivarius AD0001 | S. faecium AD1051 | S. faecium AD1050 | S. equinus AD8005 |
| 0.2% | — (min) | — (min) | 66 (min) | 118 (min) | 52 (min) |
| 0.5% | — | — | 149 | 200 | 60 |
| 1.0 | 66 | 108 | n.g | 488 | n.g |
| 1.5 | 72 | 312 | — | — | — |
| 2.0 | 116 | — | n.g | n.g | d |
| 2.5 | d *1 | n.g *2 | — *3 | — | — |
| 3.0 | d | n.g | n.g | n.g | |
| Control | | | 58 | | |

*1 d: S. mutans cells tend to be diminished until dead.
*2 n.g: Growth of S. mutans completely inhibited.
*3 Not done.

Example 2

The pre-reduced GAM broth medium (*) or VLG broth medium(**) containing hot water-soluble extracts obtained by the method described in Example 1 was inoculated by *B. gingivalis* AD50001 at the concentration of $10^7$/ml under an anaerobic condition, and was incubated at 37° C. The growth (turbidity of the culture) after 24 hours was as shown in Table 8. These results indicate clearly that the growth inhibition of *B. gingivalis* by the hot water-soluble extracts from any strain of *S. faecium*, *S. equinus*, *L. fermentum*, and *L. salivarius* was dependent on the concentration of the hot water-soluble extracts added to the growth medium. The hot water-soluble extracts obtained from any strain of *S. faecium*, *S. equinus*, and *L. salivarius* completely inhibited the growth of *B. gingivalis* at a 3% concentration of the extracts for 24 hours. The hot water-soluble extract from *L. fermentum* almost completely inhibited the growth at a 5% concentration for 24 hours.

TABLE 8

| Concentration % | Strains used for cellular extraction | | | | |
|---|---|---|---|---|---|
| | S. faecium AD1051 | S. faecium AD1050 | S. equinus AD8005 | L. salivarius AD0001 | L. fermentum AD0002 |
| 0 | | | 1.35 | | |
| 1 | 0.15 | 0.14 | 0.12 | 0.13 | 0.46 |
| 2 | 0.07 | 0.06 | 0.08 | 0.04 | 0.23 |
| 3 | <0.01 | <0.01 | <0.01 | <0.01 | 0.11 |
| 4 | <0.01 | <0.01 | <0.01 | <0.01 | 0.07 |
| 5 | <0.01 | <0.01 | <0.01 | <0.01 | <0.01 |

| * Composition of GAM broth medium GAM broth (Nissi Pharmaceutical Co. Ltd.) Code 05422 | |
|---|---|
| | (59.0 g/l) |
| Peptone | 10 g/l |
| Soy bean peptone | 3.0 |
| Proteose peptone | 10.3 |
| Digested serum powder | 13.5 |
| Yeast extract | 5.0 |
| Meat extract | 2.2 |
| Liver extract powder | 1.2 |
| Glucose | 3.0 |
| KH$_2$PO$_4$ | 2.5 |
| NaCl | 3.0 |
| Soluble starch | 5.0 |
| L-Cystein-HCl | 0.3 |
| Sodium thioglycorate | 0.3 |
| ** VLG broth medium | |
| Trypticase | 10 g/l |
| Yeast extract | 5 |
| Meat extract | 2 |

TABLE 9

| Strains | Control | S. faecium AD1051 | S. faecium AD1050 | S. equinus AD8005 | L. salivarius AD0001 | L. fermentum AD0002 |
|---|---|---|---|---|---|---|
| B. intermedius AD50002 | + | − | − | − | − | − |
| B. fragilis RIMD 0230001 | + | + | + | + | + | − |

+: turbidity >1.0
−: turbidity <0.1

| | |
|---|---|
| Resazurin | 0.001 |
| $Na_2CO_3$ | 4 |
| L-Cystein-HCl | 0.3 |
| Hemin | 0.005 |
| Menadione | 0.0005 |
| Salt solution I | 75 ml |
| $KH_2PO_4$ | 0.3 g (in 100 ml) |
| NaCl | 0.6 |
| $(NH_4)_2SO_4$ | 0.3 |
| $CaCl_2$ | 0.03 |
| $MgSO_4$ | 0.03 |
| Salt solution II | 0.3 g (in 100 ml) |
| $K_2HPO_4$ | |

Example 3

Growth inhibition of B. intermedius and B. fragilis

The growth inhibition of B. intermedius AD50002 and B. fragilis RIMD 0230001 by the hot water-soluble extracts was examined (Table 9). The experimental methods were the same as in Example 1. The concentration of the extract added was 3.0%.

B. intermedius may cause juvenile and acute periodontitis, but B. fragilis may have no relation to the disease. The hot water-soluble extracts obtained from any strain of S. faecium, S. equinus, L. salivarius, and L. fermentum inhibited the growth of B. intermedius (Table 9). However, the extracts did not inhibit the growth of B. fragilis, but this does not cause periodontitis.

Example 4

Inhibition of hemagglutination by B. gingivalis and B. intermedius.

Equal volumes of blood defibrinated and diluted 30-fold with saline, the bacterial cell suspension (ca. 2 of optical density) of B. gingivalis or B. intermedius, and the hot water-soluble extracts of the present invention were mixed on slide glasses, and the hemagglutination and time to agglutinate were observed (Table 10).

Hemagglutination is thought to be related to the adherence of bacteria to the gingivae, etc. The hot water-soluble extracts obtained from any strain of S. faecium, s. equinus, L. salivarius, and L. fermentum inhibited the hemagglutination, suggesting that the extracts may inhibit the adherence of Bacteroides to the gingivae, etc.

TABLE 10

| Strains | RBC | Control | S. faecium AD1051 | S. faecium AD1050 | S. equinus AD8005 | L. salivarius AD0001 | L. fermentum AD0002 |
|---|---|---|---|---|---|---|---|
| B. gingivalis AD50001 | H | +++ | +(+) 25(10) | +(+) 25(10) | ±(+) 25(10) | +(+) 15(15) | +(++) 10(10) |
| | | 1-2 | | | | | |
| | R | +++ 5-7 | ++ 10 | ++ 10 | ++ 20 | ++ 25 | ++ 20 |
| | S | +++ 5-7 | ++ 30 | ++ 30 | ++ 30 | ++ 40 | ± 45 |
| B. intermedius AD50002 | R | ++ 10 | − | − | − | − | − |

Concentration of the hot water-soluble extract is about 3%. Parentheses of line "H" show results in 0.75% concentration of the extracts. The upper lines show the degree of hemagglutination, and the lower lines shown the agglutination time (min).
+++: Almost all the red blood cells agglutinated. Agglutination can be seen macroscopically.
++: Agglutination can be seen macroscopically.
+: Agglutination can be seen microscopically.
±: Agglutination cannot be definitely seen.
−: No agglutination.
RBC: red blood cell.
H: Human
R: Rabbit
S: Sheep

Example 5

Antibacterial spectra

The influence of the hot water-soluble extracts obtained from the respective lactic acid bacteria of the present invention on the intestinal lactic acid bacteria and E. coli is summarized in Table 11. The concentration of the extracts was 3.0% in the test medium. The results show that the hot water-soluble extracts of the present invention have no influence on the major human intestinal bacteria.

TABLE 11

| Strains used for growth inhibition | Strains used for cellular extraction | | | | |
|---|---|---|---|---|---|
| | L. fermentum AD0002 | L. salivarius AD0001 | S. faecium AD1051 | S. faecium AD1050 | S. equinus AD8005 |
| S. faecalis | − | − | − | − | − |

TABLE 11-continued

| Strains used for growth inhibition | Strains used for cellular extraction | | | | |
|---|---|---|---|---|---|
| | L. fermentum AD0002 | L. salivarius AD0001 | S. faecium AD1051 | S. faecium AD1050 | S. equinus AD8005 |
| S. faecium | — | — | — | — | — |
| S. durans | — | — | — | + | + |
| S. avium | — | — | — | — | ++ |
| L. fermentum | — | — | — | — | — |
| L. acidophilus | — | — | — | — | — |
| L. fermentum | — | — | — | — | — |
| B. adolescentis | — | — | — | — | — |
| B. infantis | — | — | — | — | — |
| B. bifidum | — | — | — | — | — |
| B. breve | — | — | — | — | — |
| E. coli | — | — | — | — | — |

—: no inhibition
+: maximal viable cell number was counted within 12 hours as in the control, growth rate was reduced.
++: maximal viable cell number was counted within 24 hrs, as in the control, and growth rate was reduced.

Example 6

Acute toxicity (i) The hot water-soluble extracts prepared according to the above-mentioned preparation methods were intraperitoneally administered into ICR mice (6 week-old, male, average body weight $31.0 \pm 0.6$ g) in the form of an 0.5 ml saline solution containing the extracts corresponding to $9 \times 10^9$, $9 \times 10^8$, or $9 \times 10^7$ bacterial cells/mouse (10 mice in each group). The thanatobiological observation of the mice was carried out for 14 days.

The LD50 values (mg/mouse) calculated according to a Behrens-Kärber method are shown in Table 12. All the strains tested of the present invention were substantially nontoxic in the case of daily oral administration.

TABLE 12

| L. salivarius AD0001 | 6.0 mg/mouse |
|---|---|
| L. fermentum AD0002 | 10.8 |
| L. equinus AD8005 | 8.9 |
| S. faecium AD1051 | 7.3 |
| S. faecium AD1050 | 7.5 |

(ii) The heat-treated dead cells prepared according to the above-mentioned preparation methods were intraperitoneally administered into ICR mice (6 week-old, male, average body weight $30.0 \pm 0.7$ g) in the form of the dead bacterial cell suspension in 0.5 ml saline containing the extracts corresponding to $9 \times 10^9$, $9 \times 10^8$, and $9 \times 10^7$ cells/mouse (10 mice in each group). The thanatobiological observation of mice was carried out for 14 days.

The LD50 values (bacterial cell number/mouse) of the lactic acid bacterial strains, calculated according to a Behrens-Kärber method, were $6 \times 10^{13}$ cells/mouse (intraperitoneally), and all the strains were substantially nontoxic in the case of daily oral administration.

Examples in practical use

1. Tooth-paste

| | wt. % |
|---|---|
| Secondary calcium phosphate | 30–50 |
| Glycerin | 15–20 |
| Carrageenin | 0.5–20 |
| Sodium lauryl sulfate | 0.8–1.5 |
| p-Oxybutyl benzoate | 0.001–0.005 |
| Flavor | 0.5–1.5 |
| Heat-treated dead cells (autoclaved at 121° C., 15 min) of the present invention | 0.1–10 |
| Water | Remainder |
| | 100 |

2. Gargles

| | wt. % |
|---|---|
| Ethanol (90%) | 15–20 |
| Saccharin | 0.1–0.5 |
| Sodium acyltaurate | 0.2–0.6 |
| Flavor | 0.5–1.5 |
| Chlorohexidine | 0.002–0.007 |
| Hot water-soluble extracts (autoclaved at 121° C. 25 min, and centrifuged) of the present invention | 1.0–12 |
| Water | Remainder |

3. Chewing gum

| | wt. % |
|---|---|
| Gum base | 18–25 |
| CaCO$_3$ | 1–5 |
| Saccharin | 0.05–0.2 |
| Lactose | 65–75 |
| Heat-treated dead cells (autoclaved at 121° C. 15 min) of the present invention | 0.5–8 |
| | 100 |

4. Anticariogenic and antiperiodontitic foods and beverages

The heat-treated dead cells or the hot water-soluble extracts of the present invention can be used for anticariogenic and antiperiodontitic foods and beverages by the addition of 0.001% to 10% (dry weight) of the preparations into bread, cookies, candies, yogurt, fruit juice, tea, coffee, and other general foods and beverages.

We claim:

1. A biologically pure culture of microorganisms selected from the group consisting of Streptococcus faecium, Streptococcus equinus, Lactobacillus fermentum, Lactobacillus salivarius, and combinations thereof, said culture having the identifying characteristics of Streptococcus faecium FERM BP-712, Streptococcus faecium FERM BP-714, Streptococcus equinus FERM BP-716, Lactobacillus fermentium FERM BP-715, or Lactobacillus salivarius FERM BP-713, said culture having antibacterial activity against Streptococcus mutans or the genus Bacteroids, and said culture being prepared by fermentation in an aqueous nutrient medium containing assimilable sources of carbon, nitrogen and inorganic salts under aerobic and anaerobic conditions.

2. An anticariogenic or antiperiodontitic composition comprising an anticariogenically or antiperiodontitically effective amount of dead cells, water-soluble extracts, or combinations of dead cells and water-soluble extracts of microorganisms selected from the group consisting of *Streptococcus faecium* FERM BP-712, *Streptococcus faecium* FERM BP-714, *Streptococcus equinus* FERM BP-716, *Lactobacillus fermentium* FERM BP-715, *Lactobacillus salivarius* FERM BP-713, and combinations thereof, and an orally acceptable carrier.

* * * * *